(12) United States Patent
Tsai et al.

(10) Patent No.: US 12,404,254 B2
(45) Date of Patent: Sep. 2, 2025

(54) TRIS(ALKOXYCARBONYLAMINO)TRIAZINE COMPOSITION, COATING COMPOSITION COMPRISING THE SAME AND MANUFACTURING METHOD THEREOF

(71) Applicant: CHANG CHUN PLASTICS CO., LTD., Taipei (TW)

(72) Inventors: Yan-Ting Tsai, Taipei (TW); I-Chiang Lai, Taipei (TW)

(73) Assignee: CHANG CHUN PLASTICS CO., LTD., Taipei (TW)

( * ) Notice: Subject to any disclaimer, the term of this patent is extended or adjusted under 35 U.S.C. 154(b) by 0 days.

(21) Appl. No.: 17/896,332

(22) Filed: Aug. 26, 2022

(65) Prior Publication Data

US 2023/0416208 A1    Dec. 28, 2023

(30) Foreign Application Priority Data

Jun. 23, 2022   (CN) .......................... 202210719433.7
Jun. 23, 2022   (TW) ................................. 111123327

(51) Int. Cl.
  *C07D 251/54*   (2006.01)
  *C08F 8/02*     (2006.01)
  *C08F 8/44*     (2006.01)

(52) U.S. Cl.
  CPC .............. *C07D 251/54* (2013.01); *C08F 8/02* (2013.01); *C08F 8/44* (2013.01)

(58) Field of Classification Search
  CPC . C07D 251/54; C08F 8/44; C08F 8/02; C08K 5/34922; C08K 5/0025; C09D 7/63
  See application file for complete search history.

(56) References Cited

U.S. PATENT DOCUMENTS

| | | |
|---|---|---|
| 5,574,103 A | 11/1996 | Wu et al. |
| 6,506,898 B1 | 1/2003 | Flood et al. |
| 7,169,923 B2 | 1/2007 | Schneider et al. |
| 9,499,498 B2 | 11/2016 | Jacobs, III et al. |
| 10,975,237 B1 | 4/2021 | Lin et al. |
| 2009/0209701 A1 | 8/2009 | Steinmetz et al. |
| 2010/0022719 A1 | 1/2010 | Ohrbom |
| 2020/0270468 A1* | 8/2020 | Wegner ................ C09D 5/4438 |

FOREIGN PATENT DOCUMENTS

| | | | | |
|---|---|---|---|---|
| CN | 1234814 A | 11/1999 | | |
| CN | 1575285 A | 2/2005 | | |
| CN | 101490190 A | 7/2009 | | |
| CN | 101835744 A | 9/2010 | | |
| CN | 105505098 A * | 4/2016 | | |
| CN | 112480346 A | 3/2021 | | |
| DE | 10151564 A1 * | 4/2003 | ........... | C07D 251/18 |
| TW | 201439072 A | 10/2014 | | |
| WO | WO-9818856 A1 * | 5/1998 | ......... | C08G 59/5086 |

\* cited by examiner

*Primary Examiner* — James H Alstrum-Acevedo
*Assistant Examiner* — Pierre Paul Eleniste
(74) *Attorney, Agent, or Firm* — MUNCY, GEISSLER, OLDS & LOWE, P.C.

(57) ABSTRACT

The present invention provides a tris (alkoxycarbonylamino) triazine (TACT) composition, coating composition comprising the same, and manufacturing method thereof. The tris (alkoxycarbonylamino) triazine composition comprises TACT and dibutyl carbonate (DBC); wherein the DBC ranges from 2 to 11 wt % of total weight of the composition. Through the usage of the coating composition comprising the composition of the present invention, the coating film surface of the coated object can have excellent film surface appearance.

12 Claims, 2 Drawing Sheets

TRIS(ALKOXYCARBONYLAMINO)TRIAZINE COMPOSITION, COATING COMPOSITION COMPRISING THE SAME AND MANUFACTURING METHOD THEREOF

FIELD OF THE DISCLOSURE

The present invention relates to a tris(alkoxycarbonylamino)triazine (TACT) composition and the preparing process thereof. The tri(alkoxycarbonylamino)triazine composition may be used as a crosslinking agent, and in particular a crosslinking agent used for a coating composition.

BACKGROUND

Tris(alkoxycarbonylamino)triazine (TACT) is a trifunctional melamine-based crosslinking agent having a reactive carbamate functional group, which can be used as a crosslinking agent for water-based coatings and solvent-based coatings. Since the TACT-containing coating composition will not release formaldehyde during curing, and is beneficial for the hardness and chemical resistance of the coating surface of a coated object, such coating compositions containing TACT have been widely used in the field of coating.

SUMMARY OF THE DISCLOSURE

After various experiments in the invention, it is found that the process of preparing a TACT coating composition may accompany the formation of byproducts "dibutyl carbonate (DBC)". According to the present study, it is also found that the byproducts may make adverse impact on the coating surface of an object coated with the TACT coating composition regardless of their amount. For example, some pinholes may be formed or sagging may occur, so as to greatly degrade the aesthetics of the coating surface of a coated object.

In order to effectively prevent the DBC byproducts in a TACT coating composition from affecting the appearance of the coating surface of a coated object, it is found in the invention that, after many experiments, as long as the DBC content of a coating composition is controlled between 2 wt % and 11 wt %, the object coated with such a coating composition may have improved coating surface appearance.

Therefore, an objective of the invention is to provide a tris(alkoxycarbonylamino)triazine (TACT) composition, which comprises TACT and dibutyl carbonate (DBC); wherein the DBC ranges from 2 to 11 wt % of total weight of the composition.

In one or more embodiments, the DBC ranges from 3 to 8 wt % of total weight of the composition.

In one or more embodiments, the TACT has a structure as formula (I) below:

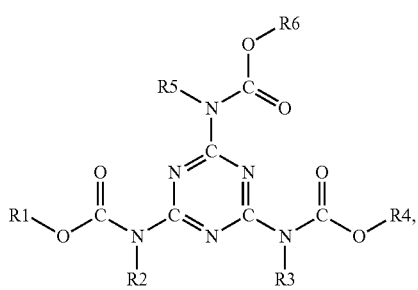

wherein each of $R_1$-$R_6$ is independently H, $NR_7R_8$ or an aliphatic group; each of $R_7$ and $R_8$ is independently H, an aliphatic group, an alkoxy group or a carbamate group.

In one or more embodiments, $R_2$, $R_3$ and $R_5$ are H.

In one or more embodiments, $R_1$, $R_4$ and $R_6$ are C1-C6 alkyl.

In one or more embodiments, a solid content of the composition is 45 to 60 wt %.

In one or more embodiments, the composition has a pH value of 4.5 to 7.0 at 25° C.

In one or more embodiments, a viscosity of the composition at 25° C. is 10 to 30 cps.

Another objective of the invention is to provide a process of preparing a composition, which comprises reacting a compound of formula (II) below

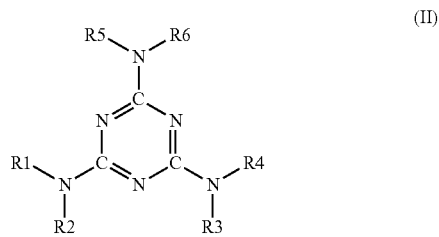

with carbonate in the presence of an alcohol and a base; wherein in formula (II), each of $R_1$-$R_6$ is independently H, $NR_7R_8$ or an aliphatic group, and each of $R_7$ and $R_8$ is independently H, an aliphatic group, an alkoxy group or a carbamate group.

In one or more embodiments, the process further comprises additionally adding DBC so that the DBC ranges from 2 to 11 wt % of total weight of the composition.

In one or more embodiments, the carbonate is dimethyl carbonate.

In one or more embodiments, the base is alkali metal alkoxide or alkaline earth metal alkoxide.

In one or more embodiments, the alkali metal alkoxide is sodium tert-butoxide or sodium methoxide.

Still another objective of the invention is to provide a coating composition, which comprises the aforementioned TACT composition as a crosslinking agent.

The efficacy of the present invention is that a coated object may have superior coating surface appearance by using the tris(alkoxycarbonylamino)triazine composition of the invention.

DETAILED DESCRIPTION

Figure 1:
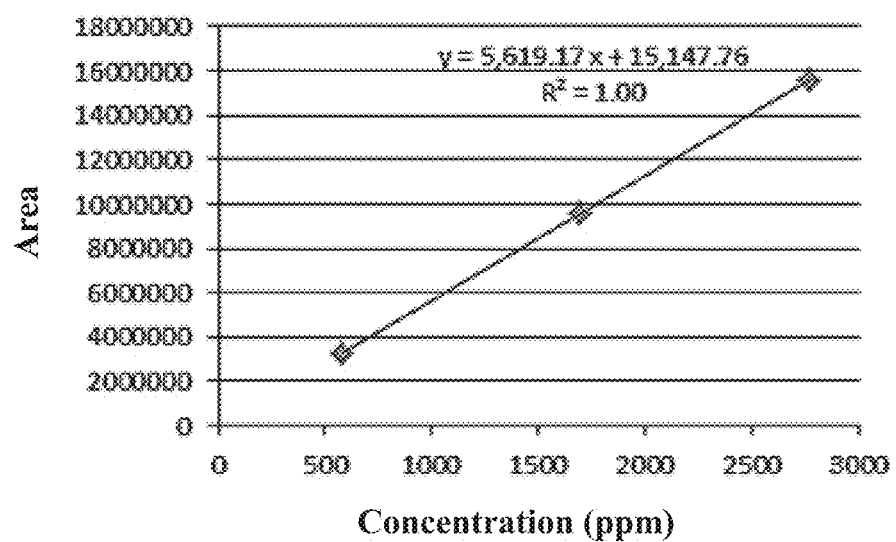
FIG. 1 is the DBC calibration curve for calculating the DBC content of a sample in accordance with the invention.

The following description should not be construed to unduly limit the present invention. It will be apparent to persons having ordinary skill in the art that various modifications and variations can be made to the embodiments described herein without departing from the spirit and scope of the invention. Thus, such modifications and variations come within the scope of the present invention.

As used herein, the article "a/an" represents one as well as more than one (i.e., at least one) syntax subject in the context.

One objective of the invention is to provide a tris(alkoxycarbonylamino)triazine (TACT) composition, which comprises TACT and dibutyl carbonate (DBC); wherein the DBC ranges from 2 to 11 wt % of total weight of the composition.

The tris(alkoxycarbonylamino)triazine (TACT) composition described herein refers to a composition comprising TACT and dibutyl carbonate (DBC) ranges from 2 to 11 wt % on the basis of total composition weight. The TACT has a structure as formula (I) below:

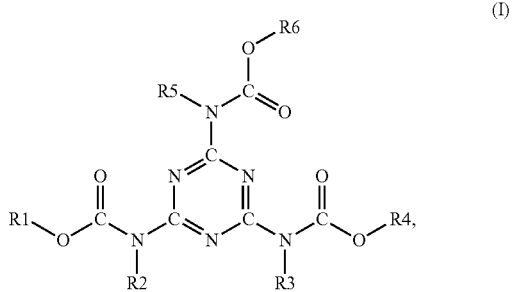

wherein each of $R_1$-$R_6$ is independently H, $NR_7R_8$ or an aliphatic group; each of $R_7$ and $R_8$ is independently H, an aliphatic group, an alkoxy group or a carbamate group.

The aforesaid "aliphatic" refers to an organic compound or a free radical with a linear, branched chain or closed ring structure, and may contain one or more saturated carbon bonds or unsaturated carbon bonds having 1 to 24 carbon atoms, for example, but not limited to, 1, 2, 3, 4, 5, 6, 7, 8, 9, 10, 11, 12, 13, 14, 15, 16, 17, 18, 19, 20, 21, 22, 23 or 24 carbon atoms.

In one or more embodiments, $R_1$, $R_4$ and $R_6$ preferably are, but not limited to, C1-C6 alkyl. The foregoing "alkyl" refers to a linear or branched saturated aliphatic group containing a single bond (alkyl) and a double bond (alkenyl), which has 1 to 12 carbon atoms, such as 1, 2, 3, 4, 5, 6, 7, 8, 9, 10, 11 or 12 carbon atoms, preferably 1 to 6 carbon atoms in the invention. The examples of alkyl groups are, but not limited to, methyl, ethyl, 1-propyl, isopropyl, 1-butyl, 2-butyl, isobutyl, tert-butyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, 1-methylhexyl, 2,2-dimethylpentyl, 3,3-dimethylpentyl, 4,4-dimethylpentyl, 1,2-dimethylpentyl, 1,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, undecyl or dodecyl, and so on.

In one or more embodiments, $R_2$, $R_3$ and $R_5$ are H.

In one or more embodiments, the DBC content ranges from 2 wt % to 11 wt % by total weight of the TACT composition, such as but not limited to the range between any two of the following values, e.g. 2 wt %, 3 wt %, 4 wt %, 5 wt %, 6 wt %, 7 wt %, 8 wt %, 9 wt %, 10 wt % or 11 wt %. 3 to 8 wt % is preferred in the invention.

In one or more embodiments, the solid content of the TACT composition is 45 to 60 wt %. The solid content is measured according to DIN EN ISO 3251 by baking the TACT composition at 105° C. for 2 hours and then evaluating the mass percentage of the remaining TACT composition relative to its initial total weight. The solid content of the TACT composition may be within the range between any two of the following values, for example, but not limited to, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt % or 60 wt %.

As used herein, the "pH value" of a TACT composition is obtained by measuring at 25° C. It is found in the invention that the composition may be degraded if the pH value of the TACT composition measured at 25° C. is too high or too low. Advantageously, the pH value of the TACT composition measured at 25° C. is controlled within a certain range. In one or more embodiments, the pH value of the TACT composition at 25° C. ranges between 4.5 and 7.0. Specific examples are, but not limited to, the range between any two of the following values, such as 4.5, 4.75, 5.0, 5.25, 5.5, 5.75, 6.0, 6.25, 6.5, 6.75 or 7.0.

As used herein, the "viscosity" of a TACT composition is obtained by measuring at 25° C. It is found in the invention that when the viscosity of the TACT composition measured at 25° C. is too high or too low, it is unfavorable for spraying a coating composition comprising the TACT composition. Hence, it is beneficial to keep the viscosity at 25° C. of the TACT composition within a certain range. In one or more embodiments, the viscosity of the TACT composition at 25° C. is 10 to 30 cps. Specifically, non-limited examples are the range between any two of the following values such as 10 cps, 12 cps, 14 cps, 16 cps, 18 cps, cps, 22 cps, 24 cps, 26 cps, 28 cps or 30 cps.

Another objective of the invention is to provide a process of preparing a composition, which comprises reacting a compound of formula (II) below

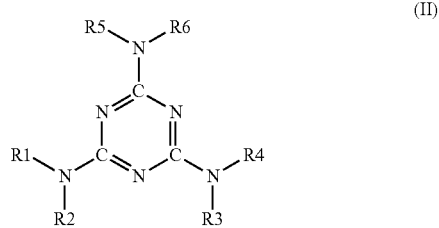

with carbonate in the presence of an alcohol and a base; wherein in formula (II), each of $R_1$-$R_6$ is independently H, $NR_7R_8$ or an aliphatic group, and each of $R_7$ and $R_8$ is independently H, an aliphatic group, an alkoxy group or a carbamate group.

In one or more embodiments, the carbonate is dimethyl carbonate.

In one or more embodiments, the alcohol is an alkanol, for example, but not limited to, methanol, ethanol, propanol, isopropanol, butanol, isobutanol, sec-butanol, tert-butanol, pentanol, isopentanol, neopentanol, tert-pentanol, hexanol, 2-methylpentanol, heptanol, octanol, 2-ethylhexanol, isooctanol, nonanol, isononanol, decanol, isodecanol, undecanol, dodecanol, tridecanol, isotridecanol, 2-methoxyethanol, 2-ethoxyethanol, 2-propoxyethanol, 2-butoxyethanol, 2- or 3-methoxypropanol, 2- or 3-ethoxypropanol, 2- or 3-propoxypropanol, 2- or 4-methoxybutanol, 2- or 4-ethoxybutanol, 3,6-dioxaheptanol, 3,6-dioxaoctanol, 3,7-dioxaoctanol, 4,7-dioxaoctanol, 2- or 3-butoxypropanol, or 2- or 4-butoxybutanol, and others. The alcohols utilized in the invention can be used alone or in combination. When mixed in use, the constituents and proportions of each alcohol in the mixture may be adjusted as desired.

In one or more embodiments, the base is alkali metal alkoxide or alkaline earth metal alkoxide. The illustrative and non-limited examples are sodium methoxide, sodium ethoxide, sodium n-propoxide, sodium isopropoxide, sodium tert-butoxide, potassium methoxide, potassium ethoxide, potassium tert-butoxide, magnesium methoxide or magnesium ethoxide, and so forth. In a preferred embodiment, the alkali metal alkoxide is sodium tert-butoxide or sodium methoxide.

It is effective to control the amount of DBC byproducts generated during the preparation of TACT compositions by adjusting the process parameters for coating compositions, especially the addition of sodium methoxide (SM) or sodium tert-butoxide (STB). In case the content of DBC is too high, generation of DBC may be suppressed by increasing the amount of SM or reducing the amount of STB. Conversely, if the content of DBC is too low, the amount of SM may be reduced or the amount of STB may be increased, resulting in the elevation of DBC. Furthermore, it can be adjusted by modifying the addition of carbonate as well. The composition contains more DBC as more carbonate is added.

Without wishing to be bound by any particular theory, it is found that in addition to the aforementioned approaches, especially by varying the addition of carbonate, SM or STB to control the amount of DBC byproducts of a TACT composition generated during the preparation process, additionally adding DBC to make the DBC content ranges from 2 to 11 wt % of total weight of the composition, may provide a coated object with superior coating surface appearance.

Therefore, the process of preparing a TACT composition may further comprise extra adding appropriate amount of DBC, making it constitute ranges from 2 to 11 wt % of total weight of the composition.

Still another objective of the invention is to provide a coating composition, which includes the described TACT composition as a crosslinking agent.

In one or more embodiment, the coating composition further comprises a polymeric resin, for example, but not limited to, functionalized or unfunctionalized acrylic, styrene acrylic, vinylacrylic, polyester, polyether, polyurethane or alkyd resin polymers, and so on.

In one or more embodiment, the coating composition further comprises a solvent to improve the solubility, dispersibility and/or storage stability of the components of the coating composition. The solvent may be water or an organic solvent. The organic solvent may be, but not limited to, glycol ethers such as butyl glycol, butyl diethylene glycol, ethoxypropanol, dipropylene glycol dimethyl ether, dipropylene glycol monomethyl ether or ethylene glycol dimethyl ether, etc.; glycol ether esters such as ethyl glycol acetate, butyl glycol acetate, butyl diethylene glycol acetate or methoxypropyl acetate, etc.; diols such as propylene glycol and the oligomers thereof, etc.; esters such as butyl acetate, isobutyl acetate or amyl acetate, etc.; ketones such as methyl ethyl ketone, methyl isobutyl ketone, diisobutyl ketone, cyclohexanone or isophorone, etc.; alcohols such as methanol, ethanol, (iso)propanol, butanol or hexanol, etc.; N-alkylpyrrolidones such as N-ethylpyrrolidone, etc.; aromatics such as toluene or aliphatics, etc.; paint solvents (S100), etc.; or any combination of the foregoing solvents.

In one or more embodiment, the coating composition further comprises catalysts, defoamers, light stabilizers, pigments, dispersants, rheology modifiers, flow agents, fillers, and others as additives.

The catalysts may be, but is not limited to, acid catalysts, base catalysts or salt catalysts. The defoamers may be, but not limited to, polyether-based defoamers, organosilicon-based defoamers or mineral oil-based defoamers. The light stabilizers may be, but is not limited to, UV protective powders, UV absorbers (UVA), quenchers, or hindered amine light stabilizers (HALS). The dispersants may be, but are not limited to, anionic wetting dispersants, cationic wetting dispersants, nonionic dispersants, amphoteric wetting dispersants, electrically neutral wetting dispersants, polymeric ultra-dispersing agents, or controllable free radical ultra-dispersing agents, etc. The rheology modifiers may be, but is not limited to, inorganic rheology aids or organic rheology aids, for example, vinylpyrrolidone copolymers, crystalline magnesium aluminum silicate hydrates, non-associative thickeners, associative thickeners, or non-ionic associative thickeners, and the like. The fillers may be, but not limited to, silica.

EXAMPLES

The present invention will be further described in detail in the following examples. However, it should be understood that these examples are illustrative for understanding of the invention only, and are not intended to limit the scope of the present invention.

Sample Preparation

Example 1

36 grams (g) of melamine (Mel) and 99.9 g of dimethyl carbonate (DMC) were added into 60 g of n-butyl alcohol (NBA) to form a reaction mixture. 625 g of n-butanol (NBA) solution containing 20% sodium tert-butoxide (STB) was then added to the reaction mixture. The reaction mixture was heated to 85° C., stirred for 180 minutes in said condition, and cooled to room temperature afterwards. Next, 300 g of 25% sulfuric acid aqueous solution was added to the reaction mixture, and stirred until the reaction mixture became homogeneous. The reaction mixture was placed still. Subsequently, the lower aqueous layer of the reaction mixture was discharged. The remaining reaction mixture was washed with water as stirring. Again, the reaction mixture was set still, and its lower aqueous layer was discharged. Then the reaction mixture was distilled under increased temperature and reduced pressure to remove excess water and NBA. NBA was further added to dilute the reaction mixture. Thereafter, the solid residue of the reaction mixture was filtered through filters. The TACT composition sample of Example 1 was obtained thereby, and DBC content detection was conducted.

Example 2

36 g of Mel and 88.8 g of DMC were added into 60 g of NBA to form a reaction mixture. Subsequently, 625 g of NBA solution containing 20% STB was added to the reaction mixture. The reaction mixture was heated to 85° C., stirred for 180 minutes in this condition, and cooled to room temperature. Next, 300 g of 25% sulfuric acid aqueous solution was added to the reaction mixture, and stirred until the reaction mixture became homogeneous. The reaction mixture was placed still. Afterwards, the lower aqueous layer of the reaction mixture was discharged. The rest of the reaction mixture was washed with water while stirring. Again, the reaction mixture was set still, and its lower aqueous layer was discharged. After that, the reaction mixture was distilled under increased temperature and reduced pressure to remove excess water and NBA. The reaction mixture was diluted with further NBA. Then the solid residue of the reaction mixture was filtered through filters. The TACT composition sample of Example 2 was obtained thereby, and DBC content detection was conducted.

Example 3

2.62 g of dibutyl carbonate (DBC) was added into 180 g of the TACT composition sample from Example 2, and stirred uniformly. The TACT composition sample of Example 3 was obtained thereby, and DBC content detection was conducted.

Example 4

10.57 g of DBC was added into 180 g of the TACT composition sample from Example 2, and stirred uniformly. The TACT composition sample of Example 4 was obtained thereby, and DBC content detection was conducted.

Example 5

180 g of the TACT composition sample from Example 1 was weighted, into which 12.45 g of DBC was added. The mixture was stirred uniformly. The TACT composition sample of Example 5 was obtained thereby, and DBC content detection was conducted.

Comparative Example 1

36 g of Mel and 95 g of DMC were added into 60 g of NBA to form a reaction mixture. Next, 586 g of NBA solution containing 14.7% sodium methoxide (SM) was added to the reaction mixture. The reaction mixture was heated to 85° C., stirred for 180 minutes in said condition, and cooled to room temperature. Then 345 g of 25% sulfuric acid aqueous solution was added to the reaction mixture, and stirred until the reaction mixture became homogeneous. The reaction mixture was placed still, and the lower aqueous layer of the reaction mixture was discharged thereafter. The rest of the reaction mixture was washed with water while stirring. Again, the reaction mixture was set still, and its lower aqueous layer was discharged. Subsequently, the reaction mixture was distilled under increased temperature and reduced pressure to remove excess water and NBA. NBA was further added to dilute the reaction mixture. Afterwards, the solid residue of the reaction mixture was filtered through filters. The TACT composition sample of Comparative Example 1 was obtained thereby, and DBC content detection was conducted.

Comparative Example 2

36 g of Mel and 111 g of DMC were added into 60 g of NBA to form a reaction mixture. 625 g of NBA solution containing 20% STB was then added to the reaction mixture. The reaction mixture was heated to 85° C., stirred for 180 minutes in said condition, and cooled to room temperature. Next, 300 g of 25% sulfuric acid aqueous solution was added to the reaction mixture, and stirred until the reaction mixture became homogeneous. The reaction mixture was placed still. Subsequently, the lower aqueous layer of the reaction mixture was discharged. The remaining reaction mixture was washed with water as stirring. Again, the reaction mixture was set still, and its lower aqueous layer was discharged. Then the reaction mixture was distilled under increased temperature and reduced pressure to remove excess water and NBA. Additional NBA was added to dilute the reaction mixture. Thereafter, the solid residue of the reaction mixture was filtered through filters. The TACT composition sample of Comparative Example 2 was obtained thereby, and DBC content detection was conducted.

Comparative Example 3

29 g of Mel and 82.9 g of DMC were added into 972 g of NBA to form a reaction mixture. Next, 87 g of 14.7% SM solid powders was added in the reaction mixture. The reaction mixture was heated to 78° C., stirred for 180 minutes in this condition, and cooled to room temperature. Subsequently, 338.2 g of 30% nitric acid aqueous solution was added to the reaction mixture, and stirred until the reaction mixture became homogeneous. After the reaction mixture was placed still, the lower aqueous layer of the reaction mixture was discharged. The rest of the reaction mixture was washed with water while stirring. Again, the reaction mixture was set still, and its lower aqueous layer was discharged. After that, the reaction mixture was distilled under increased temperature and reduced pressure to remove excess water and NBA. The reaction mixture was diluted by adding NBA. Then the solid residue of the reaction mixture was filtered through filters. The TACT composition sample of Comparative Example 3 was obtained thereby, and DBC content detection was conducted.

[Detection of DBC Byproducts]

The content of DBC byproducts in each sample was detected using an auto-sampler AOC-20i/AOC-20s (manufactured by SHIMADZU Corporation) and a flame ionization detector (FID) implementing gas chromatography. The detective conditions were set as follows:

Carrier gas: nitrogen;
Flow rate of gas: 3.0 ml/min;
Gas volume: 1 milliliter;
Temperature of injection port: 150° C.;
Temperature of detector: 200° C.;
Column: ZB-1 (1.50 mm, 0.53 mm×30 m);
Heating gradient curve of detector: after injecting a sample, keep the oven at 40° C. for 4 minutes, raise the oven temperature to 68° C. at a ramp rate of 3° C./min and to 150° C. at a ramp rate of 7° C./min, and keep at this temperature for 5 minutes;
Total runtime: 30.05 minutes.

According to the results from GC analysis, the DBC byproducts in each sample were eluted out after 24 to 26 minutes of retention time. The DBC content of each sample was further calculated by the calibration curve.

[Calculating the Content of DBC Byproducts]

1. DBC Calibration Curve Plotting

The DBC standards for 500 ppm, 1500 ppm and 2500 ppm were added to tetrahydrofuran (THF) solution respectively to formulate three DBC standard solutions, and followed by measuring area values of these DBC standard solutions in the aforementioned GC measurement conditions. According to the calculated area values and the corresponding DBC concentration values, a DBC calibration curve was plotted as shown in FIG. 1.

2. DBC Content Calculation

The sample to be tested was diluted 50 times with a THF solution, and the diluted sample was then measured in the above GC measurement conditions. As for the sample, the area value of the DBC peak at the 24 to 26 minute of residence time was calculated. The DBC content of each sample was acquired by converting the plotted DBC calibration curve.

[Test for Coating Surface Appearance]

Each sample was separately formulated into a coating composition according to the formulation in table 1 below, diluted with a Ford cup no. 4 for about 18 to 20 seconds, and coated on a substrate by spraying. After coating, the coated substrate was baked at 140° C. for 30 minutes to form a substrate with a coating of 22 to 30 μm in thickness. Examine the appearance of the coating surface.

TABLE 1

| Materials | Weight (wt %) |
|---|---|
| acrylic resin | 63 |
| acid catalyst | 1 |
| butyl ether amino resin | 12.8 |
| sample from Examples or Comparative Examples | 9 |
| paint solvent | 10.65 |
| n-butanol | 3.55 |

Experimental Results

Figure 2:
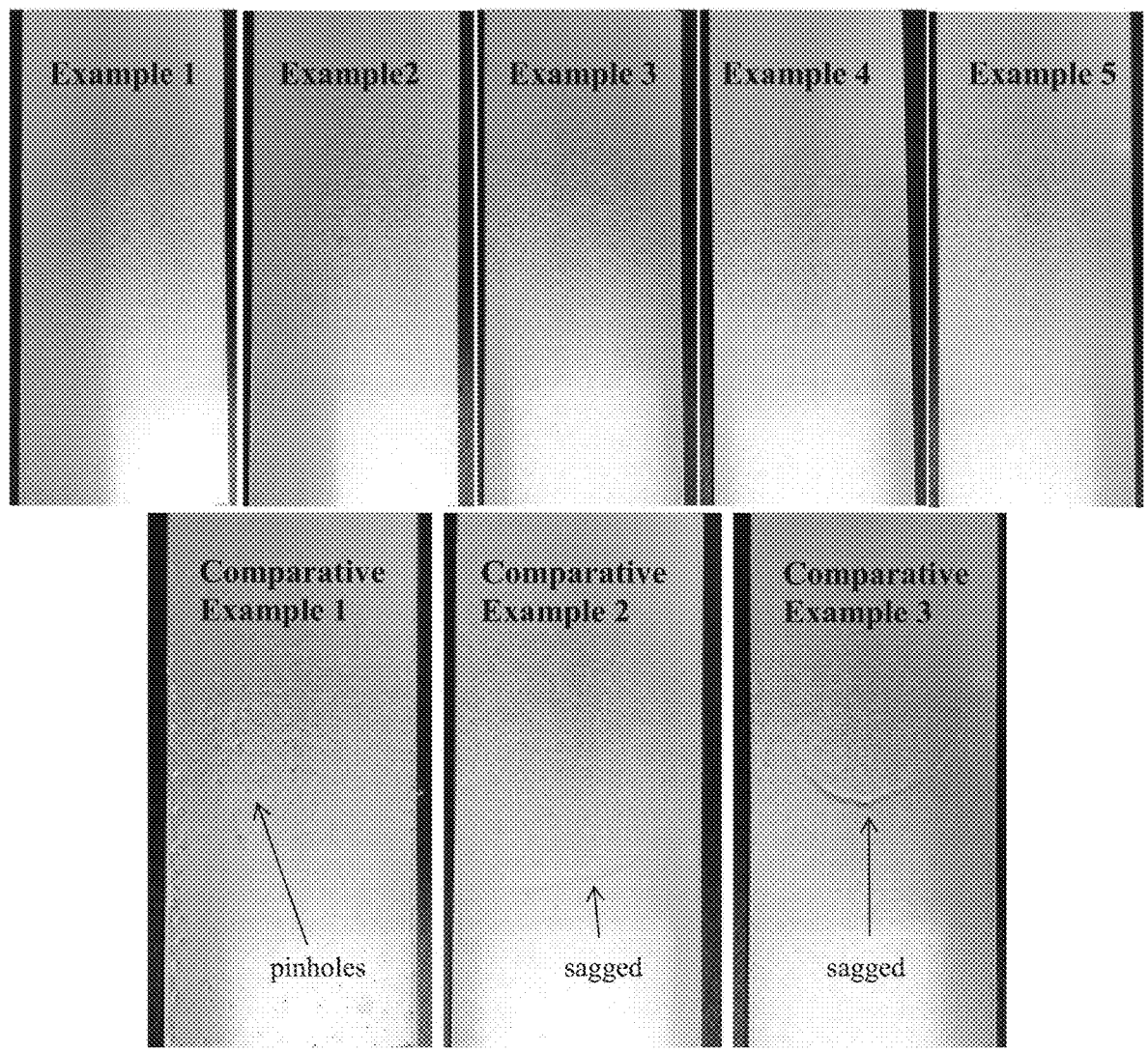
FIG. 2 shows the photograph concerning coating test results for Examples 1 to 5 and Comparative Examples 1 to 3.

Please see Table 2. Table 2 showed the physical properties, process parameters of the TACT composition samples from Examples 1 to 5 and Comparative Examples 1 to 3, and the appearance test results of the coating surface applied by the coating compositions prepared with the samples above. Reference was made in company with FIG. 2, which showed photos of Examples 1 to 5 and Comparative Examples 1 to 3 after coating tests.

the TACT compositions from Comparative Examples 1 to 3 were not controlled between 2 wt % and 11 wt % on the basis of total composition weight. As such, the coating surface that was coated with a coating composition comprising the TACT composition from Comparative Example 1 had pinholes, and the coating surfaces of Comparative Example 2 and Comparative Example 3 sagged.

In view of the description above, the tris(alkoxycarbonylamino)triazine (TACT) composition of the invention, which comprises TACT and dibutyl carbonate (DBC) ranging from 2 to 11 wt % of total weight of the composition, enables a coating composition including the inventive TACT composition to coat an object without pinholes or sagging, thereby appearing excellent coating surfaces.

All ranges provided herein are intended to include every specific range within a given range and any combination of subranges between given ranges. Furthermore, all ranges provided herein are inclusive of the endpoints of the stated range unless indicated otherwise. Thus, the range of 1-5 may include 1, 2, 3, 4, and 5, as well as the subranges of 2-5, 3-5, 2-3, 2-4, 1-4, etc.

All publications and patent applications cited in this specification are incorporated herein by reference, each of which is incorporated by reference, expressly in their respective entireties, for any purposes. In case of conflict between the specification and any publications or patent applications incorporated herein, the present specification will control.

As used herein, the terms "including", "having" and "comprising" shall be construed as open-ended and non-restrictive. The singular forms "a" "an" and "the" include plural references. The term "one or more" means "at least one" and may include a single feature or mixed/combined features.

Apart from the working examples or indicated otherwise, all values expressive of ingredients and/or reaction conditions in all cases can be modified by the term "about", and may denote other values within about 5% of a recited value.

TABLE 2

| | | Example 1 | Example 2 | Example 3 | Example 4 | Example 5 | Comparative Example 1 | Comparative Example 2 | Comparative Example 3 |
|---|---|---|---|---|---|---|---|---|---|
| Process conditions | Mel (g) | 36 | 36 | 36 | 36 | 36 | 36 | 36 | 29 |
| | DMC (g) | 99.9 | 88.8 | 88.8 | 88.8 | 99.9 | 95 | 111 | 82.9 |
| | NBA (g) | 60 | 60 | 60 | 60 | 60 | 60 | 60 | 972 |
| | 20% STB (g) | 625 | 625 | 625 | 625 | 625 | — | 625 | — |
| | 14.7% SM (g) | — | — | — | — | — | 586 | — | 87 |
| | 25% $H_2SO_4$ (g) | 300 | 300 | 300 | 300 | 300 | 345 | 300 | — |
| | 30% $HNO_4$ (g) | — | — | — | — | — | — | — | 338.2 |
| | Extra added DBC content (g) | — | — | 2.62 | 10.57 | 12.45 | — | — | — |
| Physical properties | Final DBC content (%) | 4.83 | 2.26 | 3.66 | 7.68 | 10.98 | 1.27 | 12 | 13.29 |
| | Solid content (wt %) | 51.6 | 51.4 | 49.4 | 48.1 | 48.9 | 51.1 | 51.8 | 48.2 |
| | pH (25° C.) | 6.17 | 6.02 | 6.82 | 6.75 | 6.85 | 6.85 | 6.2 | 6.62 |
| | Viscosity (cps/25° C.) | 26.22 | 24.97 | 22.65 | 18.37 | 21.25 | 24.45 | 26.8 | 18.37 |
| Comment on coating surface appearance | | Normal | Normal | Normal | Normal | Normal | Pinholes | Sagging | Sagging |

In Table 2, the comment "normal" on coating surface appearance represented there was no pinholes or sagging on a coating surface. It could be seen from Examples 1 to 5 in Table 2 that the object coated with a coating composition comprising a TACT composition, which contained 2 to 11 wt % of DBC by total composition weight, had superior coating surface appearance. On the other hand, the DBC contents of The term "essentially free" or "substantially free" as used herein means that the described feature is of less than about 2%. All elements or features expressly stated herein should not be negatively excluded from the scope of the claims.

What is claimed is:

1. A tris (alkoxycarbonylamino) triazine (TACT) composition, comprising TACT and dibutyl carbonate (DBC), wherein a weight percentage of the DBC ranges from 3.66 to 11 wt % of a total weight of the composition, wherein a solid content of the composition is 48 to 52 wt %.

2. The composition according to claim 1, wherein the weight percentage of the DBC ranges from 3 to 8 wt % of total weight of the composition.

3. The composition according to claim 1, wherein the TACT has a structure as formula (I) below:

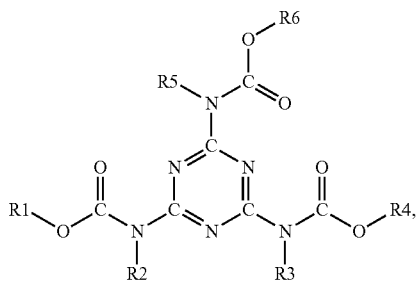

(I)

wherein each of $R_2$, $R_3$ and $R_5$ is independently H, $NR_7R_8$ or an aliphatic group; $R_1$, $R_4$ and $R_6$ are C1-C6 alkyl; each of $R_7$ and $R_8$ is independently H, an aliphatic group, an alkoxy group or a carbamate group.

4. The composition according to claim 3, wherein $R_2$, $R_3$ and $R_5$ are H.

5. The composition according to claim 1, wherein the composition has a pH value of 4.5 to 7.0 at 25° C.

6. The composition according to claim 1, wherein a viscosity of the composition at 25° C. is 10 to 30 cps.

7. A process of preparing the composition according to claim 1, comprising reacting a compound of formula (II) below

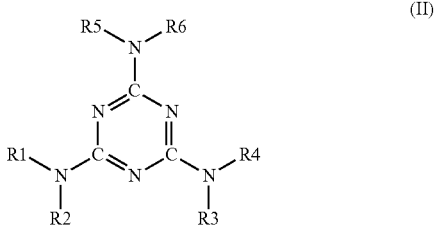

(II)

with carbonate in the presence of an alcohol and a base, wherein in formula (II), each of $R_1$-$R_6$ is independently H, $NR_7R_8$ or an aliphatic group, and each of $R_7$ and $R_8$ is independently H, an aliphatic group, an alkoxy group or a carbamate group.

8. The process according to claim 7, after completion of the reaction of the compound of formula (II) with carbonate in the presence of the alcohol and the base, further comprising additionally adding DBC.

9. The process according to claim 7, wherein the carbonate is dimethyl carbonate.

10. The process according to claim 7, wherein the base is alkali metal alkoxide or alkaline earth metal alkoxide.

11. The process according to claim 10, wherein the alkali metal alkoxide is sodium tert-butoxide or sodium methoxide.

12. A coating composition, comprising the composition according to claim 1, wherein the composition is for use as a crosslinking agent.

* * * * *